United States Patent [19]

Takemoto

[11] Patent Number: 5,071,415
[45] Date of Patent: Dec. 10, 1991

[54] NOVEL ADHESIVE MEANS FOR RELEASABLY FASTENING DISPOSABLE DIAPERS OR OTHER ARTICLES OF APPAREL

[75] Inventor: Shiro G. Takemoto, Dedham, Mass.

[73] Assignee: Kendall Company, Lexington, Mass.

[21] Appl. No.: 117,456

[22] Filed: Oct. 30, 1987

Related U.S. Application Data

[63] Continuation of Ser. No. 816,488, Jan. 6, 1986, abandoned.

[51] Int. Cl.$^5$ .................... A41B 13/02; A61F 13/16
[52] U.S. Cl. ................................................ 604/389
[58] Field of Search ............... 604/385, 386, 389, 390; 428/500; 525/98

[56] References Cited

U.S. PATENT DOCUMENTS

| | | | |
|---|---|---|---|
| 3,222,419 | 12/1965 | Jubilee et al. | 525/227 |
| 3,535,295 | 10/1970 | Davis et al. | 525/221 |
| 4,043,340 | 8/1977 | Cepuritis | 604/390 |
| 4,049,001 | 9/1977 | Tritsch | 604/374 |
| 4,074,004 | 2/1978 | Batesen et al. | 526/318.2 |
| 4,185,050 | 1/1980 | Lazear | 525/221 |
| 4,227,530 | 10/1980 | Schatz | 604/390 |
| 4,260,659 | 4/1981 | Gobran | 428/356 |
| 4,296,750 | 10/1981 | Woon et al. | 604/389 |
| 4,400,486 | 8/1983 | Iwata et al. | 525/221 |
| 4,508,864 | 4/1985 | Lee | 524/272 |
| 4,535,140 | 8/1985 | Schoenberg et al. | 526/329 |
| 4,543,099 | 9/1985 | Bunnelle et al. | 525/98 |
| 4,743,242 | 5/1988 | Grube et al. | 604/389 |

*Primary Examiner*—C. Fred Rosenbaum
*Assistant Examiner*—Sharon Rose

[57] ABSTRACT

Novel adhesive system for releasably fastening or securing superposed portions of a disposable diaper or other articles, comprising a sheet material carrying different adhesive layers on its respective surfaces, the adhesive layer on one side being characterized as having a high peel strength adapted for permanently securing the sheet material to a first portion of the diaper or other article of apparel, the adhesive layer on the other side comprising a pressure-sensitive adhesive having appreciably less peel strength and being adapted for releasably engaging an opposed portion of said article in order to secure the article on the person.

17 Claims, 1 Drawing Sheet

NOVEL ADHESIVE MEANS FOR RELEASABLY FASTENING DISPOSABLE DIAPERS OR OTHER ARTICLES OF APPAREL

This is a continuation of application Ser. No. 816,488, filed Jan. 6, 1987 and now abandoned.

BACKGROUND OF THE INVENTION

This invention is directed to an economical but efficient system for releasably fastening articles of apparel. Since it is particularly concerned with those articles generally known as disposable diapers, reference will be made thereto for purposes of illustration in the following description.

Typically, disposable diapers comprise a porous absorbent material for placement against the body and an outer liquid-impermeable liner. Obviously, means must be provided for releasably securing the diaper on the body.

The evolution of diaper closure systems has progressed through several stages from pins through permanently positioned tapes; movable tapes with the attachment area on the diaper specially reinforced to prevent tearing; then to movable tapes having a thicker attachment area with a roughened surface intended to decrease adhesion and, in turn, to prevent tearing; and finally to the so-called "repositionable tapes" currently employed on virtually all of the disposable diapers now on the market. These repositionable tapes generally are in the form of a tab engaging opposed edges adjacent one end of the diaper and adapted for releasably securing the plastic liner on the opposed end when the two ends are brought in superposition to cover the front and back lower region of the corpus.

As will be described in more detail hereinafter, these adhesive tabs are usually composed of two sheet materials, each carrying an adhesive surface. The adhesive layer on the first of these sheet materials is adapted for permanently securing this sheet material and an underlying portion of the second sheet material to the inner surface of the diaper. The second of these sheet materials is hinged with a portion underlying the first sheet material. As mentioned, the exposed portion carrying a less tacky or adherent adhesive layer is adapted for releasably engaging the plastic liner on the opposed end of the diaper when brought into superposition. Prior to use, the adhesive layer on the second sheet material may be hinged or folded into contact with the non-adhesive surface of the first sheet material, which surface then functions as a release liner protecting the repositionable adhesive layer. To facilitate this release function, the contact area on the backing of the first sheet material may contain a coating of silicone or other suitable material providing the release function. In use, the repositionable adhesive is simply peeled away from the first sheet to provide the adhesive tab for securing the diaper.

As will be appreciated, diaper closure systems such as the aforementioned repositionable tapes must possess certain criteria for optimum efficiency. On the one hand, they must possess the requisite peel adhesion, shear strength, and stability on aging to secure the diaper. On the other hand, this adhesion must not be so great as to tear the plastic liner when the tape is peeled therefrom. In essence, the adhesive must adequately secure the diaper while at the same time being alternately releasable and re-attachable a plurality of times without tearing the attachment area of the plastic liner.

Throughout the evolution of diaper closure systems from safety pins and the like, this tearing of the plastic attachment area has remained a constant problem, even though it may occur in only a small number of cases. In fact it is still regarded as the singlemost problem in the disposable diaper industry today. Consequently a "full proof" closure system is still needed.

In an effort to satisfy this need, various alternatives to the current tape systems have heretofore been considered. For example, U.S. Pat. No. 3,840,013 discloses a disposable diaper employing Velcro fasteners. However, its manufacturing costs are too great to be considered as a viable substitute.

The present invention is directed to the aforementioned problem of providing a releasable or repositionable closure system which will severely limit if not entirely preclude incidents of tearing, which closure system is both elegant and compatible with the existing diaper-making machines.

BRIEF DESCRIPTION OF THE INVENTION

In accordance with the present invention, a novel adhesive system is provided for securing superposed portions of a disposable diaper or other article of apparel. This novel adhesive system comprises adhesive patches consisting essentially of a single sheet material coated on each surface with an adhesive layer. The adhesive layer on one surface, which may be a pressure-sensitive, heat- or water-activated adhesive, is adapted to secure the patch permanently. The adhesive layer on the opposed surface possesses appreciably less peel strength and is characterized as being a pressure-sensitive adhesive adapted for releasably engaging a superposed portion of the article in such a manner that these opposed surfaces are secured together so as to withstand stress forces incidental to normal usage, but may be manually separated without tearing or rendering. The invention will be best understood by reference to the following detailed description taken in conjunction with the accompanying drawing.

DETAILED DESCRIPTION OF THE INVENTION

Figure 1:
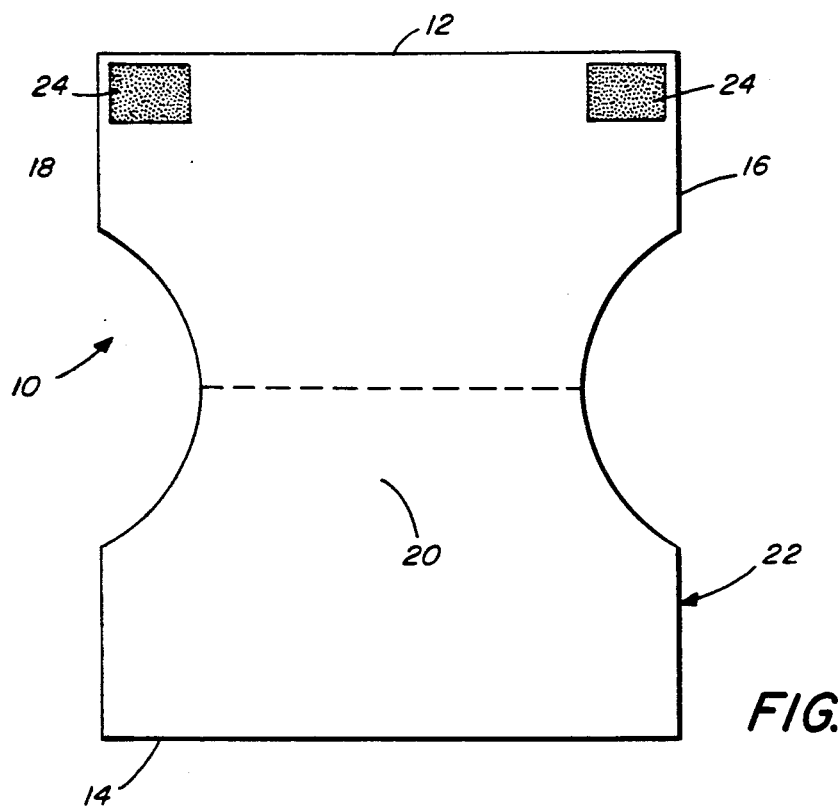
FIG. 1 is a top plan view of a conventional disposable diaper containing the novel adhesive fastening system of this invention.

Although applicable to other articles of apparel as well, the present invention is particularly directed to disposable diapers and will accordingly be described in detail by reference thereto.

As is well known, the disposable diaper market constitutes a huge and highly competitive industry. Nevertheless, virtually all disposable diapers currently commercially available are substantially similar in structure and design.

Generally, they are of an hour glass configuration adapted when folded medially to engage the lower torso with the legs extending from the curved portion.

In their simplest form, the disposable diapers may consist of a two-piece structure: an inner porous material adapted for absorbing and retaining body fluids and wastes; and an outer liquid-impermeable liner, usually a polyolefin sheet material such as polyethylene. However, in their commercial form, disposable diapers are generally of a three-piece structure: an inner liner or so-called top sheet of a non-woven material such as polyethylene, polypropylene, a polyester and the like; an outer polyolefin liner or so-called back sheet; and, sandwiched therebetween, the porous, absorbent material, generally referred to in the art as "fluff pulp", "wood fluff", or simply as "pulp".

The so-called diaper closure means for securing the diaper in place also are all essentially similar with the currently available products. To obviate the need for safety pins and the like, disposable diapers of the current generation generally employ an adhesive tab system intended to be able to releasably engage the diaper for closure a plurality of times, thereby permitting re-adjustment and/or re-diapering before the diaper is to be discarded.

Generally these adhesive tabs can be described as containing one adhesive layer adapted for permanently securing the tab to one portion of the diaper and a second "repositionable" adhesive layer which is less tacky and which is intended to releasably engage the plastic outer liner to hold the diaper in place on the body.

Although there are more than 150 U.S. patents directed to various tab structures for disposable diapers, the closure tabs currently employed generally constitute two separate elements: a first sheet material carrying the permanent adhesive layer; and a second sheet material carrying the repositionable adhesive layer. This second sheet material is secured in place by a portion thereof being placed under and adhered to the first adhesive layer, the unsecured remaining portion being flexible to constitute a foldable tab.

While not intended to be a fully comprehensive survey of the patent literature pertaining to the state of the art with respect to adhesive tabs employed with disposable diapers, the following patents are nevertheless considered to be illustrative: U.S. Pat. Nos. 4,378,800; 4,211,226; 4,182,333; 4,100,921; 4,066,081; 4,055,182; 4,047,530; 4,047,529; 4,047,528; 4,029,098; 3,948,268; 3,948,267; 3,948,258; 3,931,666; and 3,893,460.

While disposable diapers of the foregoing description are entirely satisfactory most of the time, as mentioned earlier, it is universally accepted that the major problem to overcome is the tearing of the plastic liner when the diaper is opened. Once this liner is torn, revealing the underlying porous material, re-closure is difficult and awkward to accomplish.

The present invention provides an elegant solution to this problem of tearing while at the same time simplifying construction, which in turn affords obvious significant manufacturing cost advantages.

Figure 3:
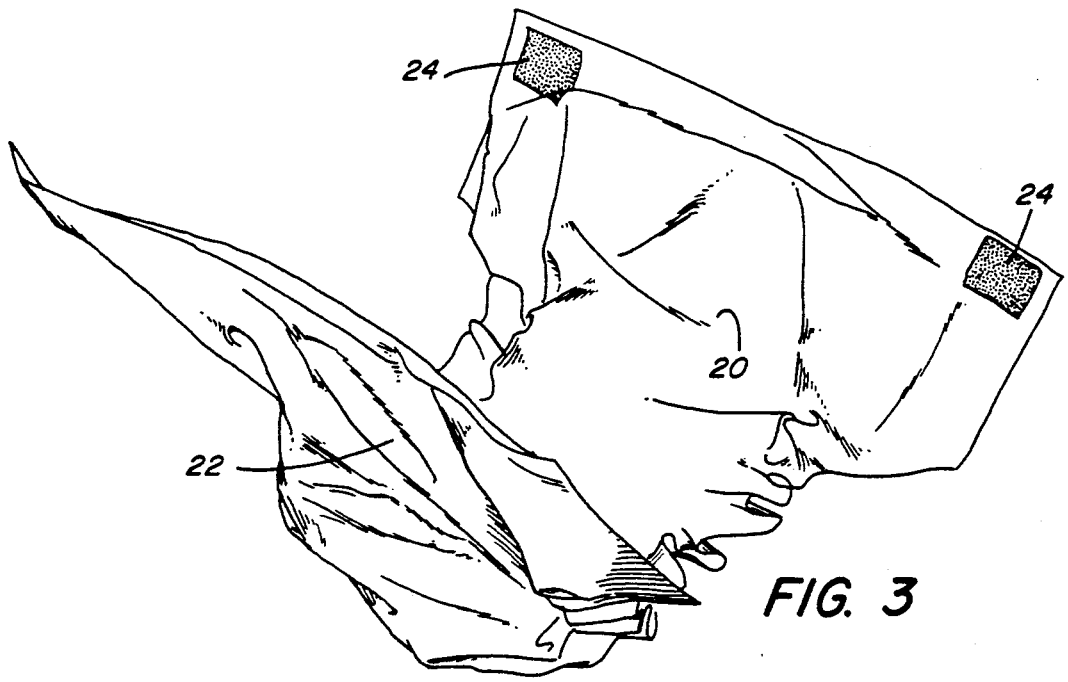
FIG. 3 is a perspective view of the diaper of FIG. 1 folded medially.

With reference now to FIGS. 1 and 3 of the drawings, the diaper 10 of this invention is shown to be of per se known configuration having ends portions 12, 14 and edge portions 16, 18 defining an hour glass-shaped article having an inner surface 20 adapted to engage the torso and an outer surface 22. In its simplest form, inner surface 20 may comprise the surface of an absorbent, porous material. However in conventional disposable diapers currently on the market, inner surface or top sheet 20 comprises a liquid-permeable flexible sheet material, outer surface or back sheet 22 comprises a liquid-impermeable sheet material, e.g. a polyolefin such as polyethylene, the absorbent material, e.g. layers of wadding, wood fluff and the like being sandwiched therebetween. As an example of disposable diapers as descibed above, mention may be made of those disclosed in U.S. Pat. No. 4,443,512 issued to Delvaux.

The novel closure system of this invention is shown to comprise a pair of adhesive patches 24 secured to the inner surface 20 adjacent opposed edges of end portion 12. While patches 24 are shown to be generally rectangular in shape, they may if desired by of other configuration, e.g. circular. However for optimum closure efficiency, it is preferred that they be generally rectangular in configuration and have a surface area on the order of one to two square inches. A typical patch may, for example, be on the order of 1 inch by 1.5 inches.

Figure 2:
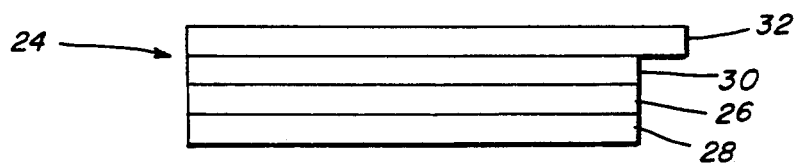
FIG. 2 is a diagramatic view of the adhesive system.

As shown in FIG. 2, patch 24 consists essentially of a sheet material 26 coated on either side with adhesive layers 28, 30. Adhesive layer 28 is a permanent adhesive adapted to secure the patch to porous material 20; while adhesive layer 30 is a repositionable adhesive adapted to releasably engage the other plastic liner 22 adjacent end portion 14 when the diaper is folded into place on the body. While not critical to the invention, it will be appreciated that a release liner or sheet 32 could, if desired, be provided over layer 30 to prevent premature and unwanted contact of the adhesive with a substrate. As illustrated, release liner 32 is shown to be of slightly greater longitudinal dimension for ease of gripping for removal. Alternatively, it is envisioned that the diaper could be packaged in its folded position with patches 24 adhered to the back sheet.

In the embodiment illustrated in the drawing, the closure system is shown to consist of a pair of opposed patches 24. Obviously modifications of design are permissible and are accordingly herein contemplated. For example, two or more patches, e.g. of smaller configuration, could be provided adjacent each of opposed edges 16, 18. In like manner, a single tape 24 could extend the width of end portion 12 to edges 16, 18 with only the portions thereof closest to the respective edges bearing an adhesive surface. However, the structure shown in the drawing is entirely sufficient for its intended purposes and is considered to be the most feasible from a cost and manufacturing standpoint.

With respect to the patches themselves, which constitute the essence of the invention, support sheet 26 may be any of the per se known materials for carrying adhesive layers and the like. It may for example be a plastic material such as cellulose acetate or a polyester such as polyethylene terephthalate, the latter being particularly efficacious. While the thickness of the support material is not critical, sheet materials on the order of a quarter of a mil thick have been found to be entirely satisfactory.

In like manner the thicknesses of the respective adhesive coatings 28, 30 may vary and may be the same or different. The selection of the particular thicknesses will be readily ascertainable by those skilled in the art. However, by way of illustration, they may be on the order of one to two mils (dry coating).

Permanent adhesive 28 may be any adhesive which will aggressively bond to the non-woven inner surface of the diaper. On the other hand, adhesive layer 30 must be repositionable. As used herein, the term "repositionable" means the ability to be positioned for closing or securing the diaper and then releasable for opening the diaper a plurality of times during at least the normal and customary usage of the diaper. In other words, it need not possess the characteristics of being repositionable an infinite or countless number of times. In the normal usage, it is contemplated that it may be necessary to re-adjust the diaper a few times when putting it on initially and then to open it a few times for inspection, e.g. to see if baby is dry. Accordingly, in the practice of this invention, it is contemplated that the adhesive closure coating should preferably be repositionable at least six times. That is to say, the pressure-sensitive adhesive for releasably engaging an opposed portion of the diaper should preferably maintain the requisite tackiness and adhesion to permit opening and securing the diaper on the order of at least six times and, most preferably, an even greater number of times.

As is well understood in the adhesive art, there is no truly efficient universal adhesive which will provide effective bonding to all substrates. Accordingly, in order to provide the closure system accomplishing the objectives to which this application is directed, the combination of substrate and repositional adhesive must be selected consistent with the objectives, as previously discussed.

Since the back sheet is conventionally a polyolefin, logic indicates that one starts with the given that the substrate, i.e. the surface of the back sheet to which the repositionable adhesive is to engage, is a polyolefin or a material which is similar to a polyolefin in the sense that its cohesive properties or behavior with respect to the repositionable adhesive are essentially the same as a polyolefin. Useful alternatives to polyolefins may be described as materials having a low energy surface, more particularly, a surface tension or energy on the order of 33 dynes/cm or less.

Accordingly, in the practice of the present invention, the surface of at least that portion of back sheet 22 which is to releasably engage the repositionable adhesive will consist of a polyolefin or a material exhibiting a cohesion with respect to the repositionable adhesive coating which is similar to polyolefins.

Typically, the back sheet comprises a single continuous sheet material. However, it is invisioned that in some instances the back sheet may comprise a first sheet material having a second sheet material laminated to its edge portions. For instance, it is understood that a disposable diaper is currently being test marketed in which a perforated breathable leg cuff is secured at either edge of the back sheet.

Critical to the present invention is providing a repositionable adhesive having the previously described releasability from the back sheet. The invention is accordingly predicated in part upon the recognition by the Applicant that polyacrylates as a class release extremely well from polyolefins, rather than aggressively bonding, as do the rubber-based adhesives. Since the polyacrylates themselves will not provide the necessary adhesion and peel strength, tackifiers need therefore be added to provide the desired adhesion for securing the diaper in its "closed" position on the body.

Accordingly, in the practice of the present invention the repositionable adhesive layer comprises a polyacrylate adhesive base containing tackifiers or adhesive agents in amounts sufficient to provide the desired balance of cohesion and releasability, that is, an adhesion which is sufficiently aggressive to maintain or secure the diaper in the closed position on the body while at the same time maintaining the releasability so that the diaper may be opened without tearing, the adhesive layer further being characterized as permitting repeated fastening, unfastenings and refastenings without losing its ability to retain the diaper in the fastened or closed position.

To those skilled in the art of adhesives, the physical prerequisites and characteristics desired for an adhesive layer are generally more relevant information than a detailed discussion of the chemical composition, e.g. monomers, tackifiers, filler and other addenda which may be in the adhesive formulation. In other words, given the desired physical prerequisites and functions contemplated for an adhesive coating, one skilled in the art may often devise the necessary formulations without the exercise of inventive faculties.

Accordingly, the respective adhesive 28, 30 will first be discussed in terms of the physical parameters and function.

As mentioned, permanent adhesive layer 28 should be an aggressive adhesive for securing the patch to the top sheet. More specifically, the adhesion to the top sheet (180° peel strength) should be on the order of at least three pounds per linear inch; and the probe tack in grams should be on the order of at least 550.

On the other hand, repositionable adhesive layer 30 should possess an adhesion generally on the order of one third that of the permanent adhesive, e.g. on the order of one to one and a half pounds per linear inch; and it should exhibit a probe tack of at least 150 grams but no greater than about 350 grams.

In a standard lap shear test (one kg. at 150° F.), the lap of a 1"×2" strip should hold for in excess of one hundred hours.

The adhesive compositions which may be employed for permanent adhesive layer 28 per se comprise no part of this invention. In general, they include those adhesives known in the art which will bond aggressively to the substrate, e.g. polyethylene, comprising the surface of the top sheet. Rubber-based adhesives are particularly efficacious. As a further illustration of suitable compositions for permanent adhesive layer 28, mention may be made of per se known resin and plasticizer modified triblock copolymers such as Kraton 1107 (trademark of Shell Oil Company for a styrene-isoprene-styrene triblock copolymer), Kraton 1102 (trademark of Shell Oil Company for a styrene-butadiene-styrene triblock), and Kraton G (trademark of Shell Oil Company); resin and plasticized copolymers of styrene-butadiene; natural rubber adhesives; polyacrylates possessing the requisite high adhesion to the top sheet substrate, etc.

As examples of suitable compositions for the repositionable adhesive layer 30, mention may be made of the class of polyacrylates which can be described as possessing good shear strength suitable for removability from the back sheet, e.g. from polyolefin films. Such a high shear polyacrylate should of course possess good removability from the polyolefin or other substrate for the back sheet. In order to achieve the proper balance of adhesion and shear strength, tackifiers, e.g. rosin ester, may be incorporated to modify the adhesion level upward without impairing the removability without tearing level. By way of further illustration, useful polyacrylate adhesives should have sufficient molecular weight, e.g. on the order of at least 500,000, to exhibit sufficient shear strength to meet the cohesive requirement derived from the copolymerization of acrylic monomers alone or with other non-acrylic monomers. As examples of useful acrylic monomers, mention may be made of those heretofore used in the adhesive industry, e.g. ethyl acrylate, 2-ethylhexyl acrylate, isooctyl acrylate, n-butyl acrylate, ethoxyethyl acrylate, etc. Other monomeric materials which may be polymerized along with one or more acrylic materials, e.g. to form a terpolymer, include vinyl acetate, acrylonitrile, ethylene, and acrylic acid.

As is understood in the art, thickeners may be found to be advisable or necessary to facilitate coating the adhesive layer(s). Suitable thickeners, e.g. acrylics such as copolymers of acrylic acid and another monomer are well known, commercially available and per se comprise no part of the present invention.

The following examples illustrate the preparation of the novel adhesive system of this invention.

EXAMPLE 1

A high molecular weight polyacrylate adhesive composition comprising: (a) 100 grams of an aqueous dispersion (approximately 55% solids content) of a tetrapolymer of 80.0 parts 2-ethylhexyl acrylate, 15.5 parts ethyl acrylate, 2.5 parts of acrylonitrile and 2.0 parts of acrylic acid; (b) 20 grams of a tackifier, FORAL 105-50WK (trademark of Hercules incorporated for a 50% solids-content anionic aqueous resin dispersion prepared from the pentaerythritol ester of hydrogenerated rosin, visc. 10–20 cps at 25° C., pH 8–10); and (c) 0.6 grams of styrene-acrylic acid copolymer thickener 68-710 (Reichold Chemicals Inc.), was coated on one surface of a double release liner, a supercalendered Kraft paper having a silicone release liner on either side (obtained from Schoeller Products under the trade designation R-coat 65ISC 60 s/s). The coating was then dried at 160° F. for about five minutes to provide a repositionable pressure-sensitive adhesive layer approximately 1.6 mils thick (when dry). A quarter mil Mylar (du Pont) polyester carrier sheet was then pressure-laminated to the dried adhesive layer by passage through a pair of superposed rubber pressure rollers. After drying, an aggressive adhesive layer was applied to the opposed surface of the Mylar carrier by coating a layer of DURO-TAK 36-6129 (trademark of National Starch and Chemical Corporation for a pressure-sensitive, rubber-based solution, 55% solids, visc. 3,000 cps.) and then drying at 160° F. for about five minutes to provide an adhesive layer approximately 1.6 mils thick. The resulting two-sided tape was then cut into one-inch strips and rolled up with the aggressive adhesive layer adjacent the free release liner.

EXAMPLE 2

Example 1 was repeated, employing 100 grams a polyacrylate adhesive formulation according to Example 1 of U.S. Pat. No. 4,204,023 issued to Witt May 20, 1980 to which was added 15 grams of FORAL 105-50WK and 0.6 grams of 68-710 thickener.

Adhesive patches prepared in accordance with the foregoing illustrative examples were tested on commercially available disposable diapers, as shown in the drawings. In these tests, patches approximately 1"×1.5" were applied as shown with the aggressive adhesive bonded adjacent opposed edges at one end of the top sheet and the release liner was removed to reveal the repositionable adhesive layer. They were subjected to repeated openings and closings by attachment to the back sheet far in excess of what would be required in usage, e.g. twenty or more times. In every instance they exhibited sufficiently aggressive bonding to secure the diaper and in no instance was any tearing of the back sheet evidenced.

In the foregoing description of the invention, the adhesive system has been described as what may be termed a two-faced adhesive patch, i.e. a laminar structure with the carrier or support element sandwiched between two outer adhesive layers, one being aggressive for permanent bonding to the top sheet of the disposable diaper, the outer being a repositionable adhesive for releasably engaging the back sheet.

Because of its simplicity in manufacture, this structure is preferred. However, it is contemplated that the adhesive system may be in the form of tabs or "ears" extendable beyond the periphery of the diaper body such as the various configurations of this description described in the patent literature.

While reference has been made throughout to disposable diapers, the articles to which this invention is primarily directed, it will further be appreciated that the invention is also applicable to various other inexpensive and/or disposable articles where repositionable adhesives are desired. For example, disposable liquid-impermeable paint garments are known in the art. They may be in the form of jackets, smocks and the like for use in the home, laboratory, commercial establishments such as auto body shops and the like.

From the foregoing description it will thus be seen that the present invention solves a long-felt need with disposable diapers and the like by providing a simple, inexpensive and highly efficacious adhesive system for releasably securing the article.

Since various changes may be made without departing from the spirit and scope of the invention as recited in the appended claims, it is intended that the foregoing description be taken as illustrative and not in a limiting sense.

We claim:

1. In a disposable article of apparel having opposed edge portions, an inner surface adapted to be positioned against the body and an outer surface comprising a tearable plastic material having a surface tension no greater than about 33 dynes/cm, said article having secured to said inner surface of one said edge portion at least one repositionable pressure-sensitive adhesive layer adapted for releasably engaging said plastic material of the other said edge portion when the other of said opposed edge portions is placed in superposition therewith, whereby to releasably secure said opposed edge portions;

the improvement wherein said adhesive layer comprises the free outer layer of an adhesive patch consisting of a sheet material carrying said repositionable adhesive layer on one surface thereof and a permanent adhesive layer on the opposed surface, said patch being adhered to said article of apparel by means of said permanent adhesive layer, said repositionable adhesive layer comprising a blend of polyacrylate and tackifier characterized as being sufficiently aggressive to secure said opposed edge portions but being releasable without tearing said superposed plastic material to which it is adhered, said adhesive layer further being characterized as possessing a 180° peel strength adhesion of from about one to about one and a half pounds per linear inch and a probe tack of from about 150 to about 350 grams.

2. An article as defined in claim 1 wherein said plastic material is a polyolefin.

3. An article as defined in claim 1 wherein said disposable article of apparel is a disposable diaper.

4. An article as defined in claim 3 wherein said plastic material is a polyolefin.

5. An article as defined in claim 3 wherein said polyacrylate repositionable pressure-sensitive adhesive has a molecular weight of at least 500,000.

6. An article as defined in claim 5 wherein said polyacrylate is derived from the polymerization of at least one acrylic monomer selected from the group consisting of ethyl acrylate, 2- ethylhexyl acrylate, isooctyl acrylate, n-butyl acrylate and ethoxyethyl acrylate.

7. An article as defined in claim 6 wherein said polyacrylate comprises the tetrapolymer of 2- ethylhexyl acrylate, ethyl acrylate, acrylonitrile and acrylic acid.

8. A disposable diaper having opposed end and edge portions, a porous inner surface or top sheet and a tearable liquid-impermeable outer surface or back sheet comprised of a polyolefin or other plastic material having a surface tension no greater than about 33 dynes/cm, at least one repositionable adhesive layer being positioned on said inner surface adjacent opposed edge portions at one end thereof, said adhesive layer being adapted for releasably engaging said outer surface when brought in superposition therewith whereby to secure said diaper on the body, each said adhesive layer being characterized as being sufficiently aggressive to alternately secure, release and resecure said diaper on the body a plurality of times, but being releasable from the adhered portion of said tearable outer surface without tearing, each said adhesive layer comprising a blend of polyacrylate and tackifier possessing a 180° peel strength adhesion of from about one to about one and a half pounds per linear inch and a probe tack of from about 150 to about 350 grams, each said adhesive layer comprising the free outer surface of an adhesive patch consisting of a sheet material carrying said respositionable adhesive layer on one surface thereof and a permanent adhesive layer on the opposed surface, said patch being adhered to the inner surface of said diaper by means of said permanent adhesive layer.

9. A disposable diaper as defined in claim 8 wherein said outer surface comprises a polyolefin.

10. A disposable diaper as defined in claim 9 wherein said polyolefin is polyethylene.

11. A disposable diaper as defined in claim 10 wherein said polyacrylate adhesive has a molecular weight of at least 500,000.

12. A disposable diaper as defined in claim 11 wherein said polyacrylate is derived from the polymerization of at least one acrylic monomer selected from the group consisting of ethyl acrylate, 2- ethylhexyl acrylate, isooctyl acrylate, n- butyl acrylate and ethoxyethyl acrylate.

13. A disposable diaper as defined in claim 12 wherein said polyacrylate comprises the tetrapolymer of 2- ethylhexyl acrylate, ethyl acrylate, acrylonitrile and acrylic acid.

14. A disposable diaper as defined in claim 8 wherein each said adhesive layer is contained on a carrier sheet material adhesively secured to said inner surface.

15. A disposable diaper as defined in claim 8 wherein each of said adhesive layers is from about one to about two mils thick.

16. A disposable diaper having opposed end and edge sections, an inner surface comprising a liquid-permeable sheet material and an outer surface comprising a liquid-impermeable tearable polyolefin sheet material, an adhesive patch being secured to said inner surface adjacent each of the opposed edges at one of said end sections, each said patch consisting essentially of a support sheet having on one surface thereof an adhesive layer aggressively adhering said patch to said inner surface, the opposed surface of said patch carrying a repositionable adhesive layer adapted for releasably engaging said outer surface when said diaper is folded medially to bring an area of said outer surface in superposition therewith, said repositionable adhesive layer being characterized as being sufficiently aggressive to engage said superposed outer surface to secure said diaper on the body but being releasable therefrom by pulling without tearing said outer surface to which it was adhered, said adhesive layer comprising a blend of polyacrylate and tackifier.

17. A disposable diaper as defined in claim 16 wherein said repositionable adhesive layer is further characterized as possessing a 180° peel strength adhesion of from about one to about one and a half pounds per linear inch and a probe tack of from about 150 to about 350 grams.

* * * * *